US008007445B2

(12) United States Patent
Harttig

(10) Patent No.: US 8,007,445 B2
(45) Date of Patent: Aug. 30, 2011

(54) ANALYTICAL AID

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 195 days.

(21) Appl. No.: 11/409,821

(22) Filed: Apr. 24, 2006

(65) Prior Publication Data

US 2006/0247555 A1 Nov. 2, 2006

(30) Foreign Application Priority Data

Apr. 22, 2005 (EP) .................................... 05008933

(51) Int. Cl.
*A61B 5/00* (2006.01)
*A61B 17/14* (2006.01)
*A61B 17/32* (2006.01)

(52) U.S. Cl. ....................................... 600/583; 606/181

(58) Field of Classification Search .................. 600/573, 600/576, 583–584; 606/181–183
See application file for complete search history.

(56) References Cited

U.S. PATENT DOCUMENTS 4,442,836 A 4/1984 Meinecke et al.
4,648,408 A 3/1987 Hutcheson et al.
5,554,166 A 9/1996 Lange et al.
6,136,013 A * 10/2000 Marshall et al. .............. 606/167
6,315,738 B1 * 11/2001 Nishikawa et al. ........... 600/583
6,497,845 B1 12/2002 Sacherer
7,223,248 B2 * 5/2007 Erickson et al. .............. 600/584
2002/0052618 A1 5/2002 Haar et al.
2003/0050573 A1 3/2003 Kuhr et al.
2003/0211619 A1 11/2003 Olson et al.
2003/0212347 A1 11/2003 Sohrab
2004/0064068 A1 4/2004 DeNuzzio et al.
2005/0027211 A1 * 2/2005 Kuhr et al. .................... 600/583
2005/0283094 A1 * 12/2005 Thym et al. ................... 600/583

FOREIGN PATENT DOCUMENTS

CA 2 311 496 6/1999
DE 35 15 420 A1 10/1986
EP 1 508 304 A1 8/2003
WO WO 86/00513 1/1986
WO WO98/48695 11/1998

* cited by examiner

*Primary Examiner* — Max Hindenburg
*Assistant Examiner* — H. Q. Nguyen
(74) *Attorney, Agent, or Firm* — Bose McKinney & Evans LLP

(57) ABSTRACT

The present invention relates to an analytical aid comprising a base body, a lancet and a test element. The base body comprises two subsidiary bodies hingedly connected to one another, the first subsidiary body carrying the lancet with lancet tip, and the second subsidiary body carrying the test element with test field and a sample application site. In an unused position of the analytical aid, the subsidiary bodies are arranged substantially in a common plane and the lancet is protected by a seal connected to the first subsidiary body and is separated from the test field of the test element. The two subsidiary bodies are pivotable relative to one another out of the common plane and the seal is openable so that the lancet tip is released for use.

25 Claims, 15 Drawing Sheets

15
5
4
10
22
23

21,26
15
25
22
23
19
27
24

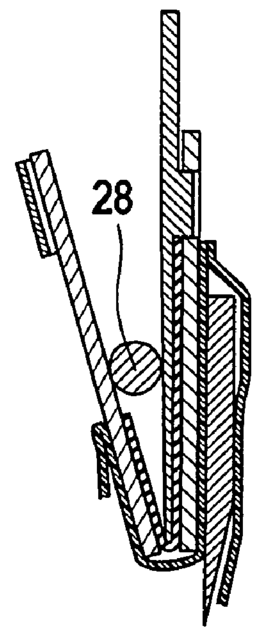
Fig. 3d
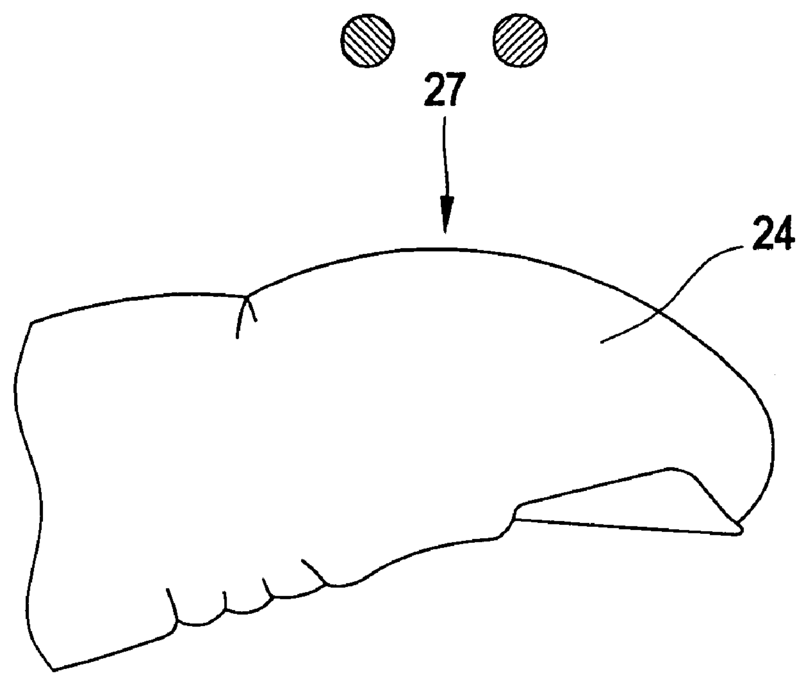

21,26
28
18

9
27
24

31
1
25
15
6
4
10
3
7
30
16
33
5
18
32
34

35
36

30
38
36

17
34
18
24

1

40
8

ANALYTICAL AID

RELATED APPLICATIONS

This application claims priority to European Patent Application No. EP 05 008 933.3, filed Apr. 22, 2005.

BACKGROUND

The present invention relates to an analytical aid comprising a lancet and a test element, a method for producing such an analytical aid, and a method for analysing a sample using such an analytical aid.

In clinical diagnostics, examination of blood samples or of interstitial fluid permits early and reliable detection of pathological conditions and also specific and reliable monitoring of physical states. Medical diagnostics entails obtaining a sample of blood or of interstitial fluid from the individual who is to be examined.

To obtain the sample, the skin of the person to be examined can be punctured, for example at the finger pad or ear lobe, with the aid of a sterile, sharp lancet in order to obtain a small amount of blood or interstitial fluid for the analysis. This method is particularly suitable for sample analysis that is carried out directly after the sample has been obtained.

In the area of home monitoring in particular, i.e., where persons without specialized medical training carry out simple analyses of blood or of interstitial fluid themselves, and particularly for diabetics taking blood samples on a regular basis, several times a day, to monitor their blood glucose concentration, lancets and associated devices (puncturing aids) are sold that allow samples to be taken with the least possible discomfort and in a reproducible manner. Such lancets and devices (puncturing aids) are the subject matter of, for example, WO-A 98/48695, EP-A-0 656 970, U.S. Pat. Nos. 4,442,836 or 5,554,166.

Self-monitoring of blood glucose levels is a method of diabetes control that is now applied worldwide. Blood glucose monitors in the prior art typically include an analysis device (meter) into which a test element (test strip) is inserted. The test element is brought into contact with a droplet of a sample which has previously been obtained by means of a puncturing aid, for example from the pad of a finger. Analytical test elements of this kind are known from CA 2,311,496, for example. The analytical test element described there contains a detection element and a channel that permits capillary transport of fluid, so that when the test element comes into contact with a droplet of blood at the sample application site, blood is brought into contact with the detection element and a detectable reaction with the analyte takes place.

The numerous system components needed for self-monitoring of blood glucose (lancet, puncturing aid, test element and analysis device) take up a great amount of space and entail relatively complex handling. There are now also systems with a higher degree of integration and, consequently, easier handling, for example ones in which the test elements are stored in the analysis device and made available from this for the measurement. A next step in miniaturization may be achieved, for example, through the integration of several functions or functional elements in a single analytical aid (disposable). For example, the operating sequence can be greatly simplified by suitable combination of puncturing procedure and sensor-based analyte concentration detection on one test element.

U.S. publication no. 2003/0050573 has as its subject matter an analytical aid with lancet and test element. The lancet comprises a lancet needle with a tip, and a lancet body which completely surrounds the lancet needle at least in the area of the tip, the lancet needle being displaceable relative to the lancet body. At least in the area of the tip of the needle, the lancet body is made of an elastic material into which the lancet needle is embedded. The analytical test element is connected fixedly to the lancet body.

U.S. publication no. 2003/0211619 relates to bands with testers arranged thereon which each comprise a test strip sensor and a micro needle. The proximal end of each tester is secured on the band, so that the tester, when it is not sealed, can be bent away from the edge.

U.S. Pat. No. 4,648,408 concerns a blood-testing device made up of three plastic blocks which can be folded together and on which, in addition to a needle, there are also a reagent strip and a disinfectant.

U.S. publication no. 2002/0052618 A1 has as its subject matter an analytical aid with integrated lancet in a lancet body, the lancet body being connected movably, for example tiltably or pivotably, to a frame part of a test element, such that the lancet can adopt a storage position and a puncture position, the lancet in the storage position being substantially parallel to the plane of the test element and, in the puncture position, being substantially orthogonal to the plane of the test element.

U.S. publication no. 2004/0064068 A1 relates to a lancet arrangement integrated into a measurement strip. According to one embodiment described (FIG. 3), the angle between the movement of the lancet and the plane of the measurement surface of the measurement strip is variable.

U.S. publication no. 2003/0212347 A1 concerns devices comprising at least one skin-puncturing element, a biosensor, and a liquid transport path between the skin-puncturing element and the biosensor. According to one embodiment described (FIG. 8), such a device is designed in such a way that the skin-puncturing element (lancet) can be turned away from the plane of the biosensor about a pivot axis.

EP 1 508 304 A1 relates to a medical device having an upper and a lower flexible sheet, a lancet body and a test strip. The lancet body has an opening into which a puncture element extends. The reaction zone of the test strip is in contact with the opening in the lancet body. This has the disadvantage that some of the test chemicals present on the reaction zone can reach the puncture element and that sterilizing of the puncture element is not possible without undesired sterilizing of the reaction zone.

These analytical aids known from the prior art are complicated in structure, in most cases with a large volume, are impractical in use, and are expensive to produce.

A large number of problems have to be addressed in the production of analytical aids. The lancet has to be sterilized, and the sterile condition of the lancet has to be guaranteed for the period of use of the analytical aid. The function and action of the test chemicals present in the test field of the test element may be adversely affected by the known sterilization methods. Sensitive chemical or biological substances may be damaged. Therefore, the test chemicals should to the extent possible not be exposed to the sterilization method for the lancet. For use of the analytical aid, the sterile protection must also be able to be safely removed without risk of injury to the user.

SUMMARY OF THE INVENTION

The present invention addresses the disadvantages of the prior art noted above.

In one form thereof, the present invention provides an analytical aid comprising a base body including first and second (subsidiary) bodies hingedly connected to one another. That is, the first and second bodies are connected to one another by a hinge-like connection. The first body carries a lancet having a lancet tip and the second body carries a test element having a test field and a sample application site. The analytical aid has an unused position in which the first and second bodies are arranged substantially in a common plane and in which the lancet is protected by a seal connected to the first body and is separated from the test field. The first and second bodies are pivotable relative to one another from the unused position, and the seal is openable to release the lancet tip for use.

This analytical aid (a synonymous term for which is “disposable”) combines the three functions of puncturing, sample application, and test chemistry for analyzing the sample.

In one aspect, the base body of the analytical aid serves as a carrier for the lancet. It comprises two subsidiary bodies and is preferably strip-shaped when the two subsidiary bodies are located in one plane, that is to say when they are not pivoted relative to one another. As regards the dimensions of such a strip-shaped analytical aid, it is possible, by way of example only, to choose a length of about 38 mm and a width of about 9 mm. At the end of the second subsidiary body with the sample application site, the corners can be cut at an angle of about 45° over about 2 mm. If a cover is provided, it can extend beyond these cut corners so that it is easy to grip.

The lancet is provided for puncturing the skin of a patient at suitable locations with the lancet tip in order to obtain a blood sample or a sample of interstitial fluid. The lancet can be a round, needle-shaped or flat lancet. Round, needle-shaped lancets are normally produced from wire sections which are provided with a sharp tip by grinding. Flat lancets are normally produced by punching, etching or laser-cutting from flat steel. The lancet in the analytical aid is secured on the first subsidiary body. The lancet tip protrudes beyond the edge of the first subsidiary body at least by the depth of insertion necessary for puncturing the skin. The lancet is secured on the first subsidiary body preferably by adhesive bonding, in particular with the aid of hot-melt adhesive or by welding it or melting it in. The first subsidiary body can be structured in advance such that it has recesses for receiving the lancet. Such a structure can be generated, for example, by embossing or by adhesive application of a film with corresponding recesses.

The lancet fixed on the first subsidiary body, or at least the lancet tip, is protected by a seal for as long as the analytical aid is in an unused state. By means of the seal, at least the lancet tip can be kept sterile (germ-free) in the unused state until immediately before use. Moreover, the seal prevents contamination of the lancet tip by components of the test chemicals located in the test field of the test element, since the seal completely separates the lancet from the test field.

The test element is used for the analysis of the blood sample or sample of interstitial fluid. It comprises at least one test field with a test chemical adapted to the sample that is to be tested. The test element is arranged on the second subsidiary body of the analytical aid. The test element or second subsidiary body can also comprise a means for transporting the sample from a sample application site, which serves to take up the sample from the skin punctured by the lancet, to the test field on which the analysis of the sample is performed.

The two subsidiary bodies are hingedly connected, i.e., connected to one another via a hinge-like connection. The hinge-like connection permits a pivoting of the two subsidiary bodies relative to one another. In the unused state of the analytical aid according to the invention, the two subsidiary bodies lie substantially in a common plane. In this arrangement referred to below as the starting position, the two subsidiary bodies form a substantially flat base body and are not pivoted relative to one another ($\alpha=0°$). The lancet then bears on the flat base body and is protected by the seal, so that undesired injury by the lancet tip is avoided. When the analytical aid is put to use, the two subsidiary bodies are pivoted relative to one another, as a result of which, among other things, the lancet tip can be released for use. In this case, the seal is opened upon pivoting of the two subsidiary bodies. The opening of the seal is effected, for example, by tearing as a result of a tensile force acting on the seal during pivoting of the subsidiary bodies, or by the seal being cut by the lancet tip. Another possibility is that, during the pivoting of the subsidiary bodies, the seal is severed at its site of connection to the subsidiary bodies (e.g. adhesive connection) and the lancet tip is thus released. However, the seal can also be opened when inserting the analytical aid into an analysis device, by a means provided for this purpose (e.g. blade), or it can be opened by the user prior to insertion in the analysis device.

In certain embodiments of the present invention, the hinge-like connection is configured such that the subsidiary bodies can be pivoted relative to one another from the starting position by an angle $\alpha$ of at least 90° and up to 180°. In the case of pivoting by $\alpha=180°$ from the starting position, the two subsidiary bodies are folded together, that is to say arranged alongside and parallel to one another and connected to one another at the hinge-like connection (hingedly connected).

As soon as the two subsidiary bodies are pivoted relative to one another and the lancet tip is released, the lancet tip can be used to puncture the skin (for example the finger pad) of a patient in order to obtain a sample of blood or interstitial fluid. The subsidiary bodies of the analytical aid can then be pivoted back into the starting position so that the lancet once again bears on the base body and a risk of injury is substantially avoided. To take up the sample, the sample application site of the analytical aid can then be guided towards the sample (for example a droplet of blood) in order to apply the latter to the test element, if appropriate with the help of the means for transporting the sample to the test field, where it reacts with the test chemical, and in order to analyze it there.

Certain embodiments incorporating the present invention have the following advantages among others:

- The analytical aid has a simple and compact structure with a small number of components, and it combines a large number of functions. It is suitable for use in compact automated analysis devices.
- The lancet is sealed in a sterile state by the seal, so that microorganisms cannot reach the lancet tip until immediately before the lancet is used. The seal also protects it from contact with the test chemical.
- The two subsidiary bodies, of which one carries the lancet and the other carries the test element, can be prefabricated separately from one another. The lancet can therefore be sterilized before the two subsidiary bodies are connected via the hinge-like connection (for example by gamma radiation), so that the test chemical is not exposed to the possibly damaging sterilization.
- The analytical aid can have a shape similar to conventional test strips, such that it can be used in a conventional analysis device adapted to the structure and mode of operation of the analytical aid.
- The person using the analytical aid is provided with considerable protection against inadvertent injury on the lancet tip. The analytical aid permits a high speed of puncture with the lancet tip and a short dwell time of the lancet tip in the skin, so that the puncturing causes little pain.

According to a particular embodiment of the present invention, the hinge-like connection is a flexible strip that connects the two subsidiary bodies to one another. The flexible strip can be bonded or welded against the subsidiary bodies bearing with their edges on one another in one plane. For example, it can consist of an adhesive tape. The hinge-like connection can also be formed by the seal alone. A further possibility is to design the hinge-like connection as a film hinge. Film hinges or film joints are tape hinges and have no mechanical parts. A film hinge is a flexible, thin-walled hinge groove between two parts that are to be connected.

The sample application site can be arranged in the area of an end of the second subsidiary body remote from the hinge-like connection. The sample application site is in this way located on an exposed and thus readily accessible end of the base body when the subsidiary bodies are not pivoted relative to one another and thus lie in one plane.

The lancet tip may protrude beyond the first subsidiary body in the area of the hinge-like connection. In this way, it bears on the base body or on the second subsidiary body when the analytical aid according to the invention is in the starting position, and it protrudes, in a readily accessible manner ready for puncturing, beyond the edge of the first subsidiary body as soon as the subsidiary bodies are pivoted away from the starting position about the hinge-like connection by an angle $\alpha \geqq 90°$. The lancet tip can therefore be oriented substantially parallel to the second subsidiary body in the unused state of the analytical aid.

According to another particular embodiment of the present invention, the seal is a pocket-like guard which partially or completely encloses the lancet in the unused state of the analytical aid. In the case of only partial enclosure, at least the lancet tip is closed off in a sterile state by the pocket-like guard. The pocket-like guard is formed, for example, by a thin film encapsulating the lancet and in particular the lancet tip, the film being connected along the lancet in order to form a kind of pocket. The film is, for example, partially sealed onto the first subsidiary body before the lancet is fitted, and, after the lancet has been fitted, is folded over the lancet tip and secured, for example with adhesive, on the sealed-on part of the film, such that the lancet tip is located in a pocket-like guard formed from the film. During its fitting, the lancet is preferably rotated about its longitudinal axis such that a face of the ground edge of the lancet is oriented as far as possible perpendicularly with respect to the hinge-like connection and points away from it.

The seal at the lancet tip is preferably connected fixedly to the second subsidiary body. In the case of a pocket-like guard, the latter can be connected to the second subsidiary body, for example via its front edge at the lancet tip. In this way, the seal, which is secured on the first subsidiary body and is also connected to the second subsidiary body in the area of the lancet tip, spans the hinge-like connection between the two subsidiary bodies. It can be fully stretched out in the starting position and, upon pivoting of the subsidiary bodies from the starting position, stretched across the edges of the subsidiary bodies at the hinge-like connection such that it tears in the area of the lancet tip and releases the latter for use. For this purpose, the seal, at least in the area of the lancet tip, is made from a brittle material. Brittle in this context means that the material has a small elongation at break and low tear propagation resistance. A suitable material is, for example, foamed oriented polypropylene (OPP) from the company Huhtamaki Deutschland GmbH & Co. KG in Ronsberg (Allgau). A smooth cutting-through of the seal is ensured by the choice of material and the orientation of the ground edge of the lancet.

Moreover, in a particular embodiment of the invention, the hinge-like connection is formed by the seal.

In certain embodiments of the present invention, the test element comprises means for electrochemical or optical analysis of a sample present on the test field. The sensor-based detection of an analyte on a test element by means of photometric or electrochemical methods takes place according to known methods. In the case where electrochemical detection of an analyte in the sample is intended, the second subsidiary body is provided with electrical connections. These electrical connections can be produced, for example, by sputtering on of a gold layer and by forming electrodes, conductor tracks and contact pads from the gold layer by means of laser ablation. The electrodes can be covered over by reagent layers and masking layers. In the case where optical detection of an analyte in the sample is intended, the second subsidiary body is equipped with the necessary optical elements, for example with a transparent window.

According to one embodiment of the present invention, the first subsidiary body of the analytical aid according to the invention has a recess for engagement of a guide element belonging to an analysis device, via which the analytical aid is guided to a sample collection location for puncture with the lancet and for application of the sample. With the help of the guide element engaging in the recess, the analytical aid can be guided into the appropriate position in the analysis device without manual intervention by the user.

The analytical aid according to one embodiment of the invention also comprises a cover which is arranged on the analytical aid and which is connected fixedly to the first subsidiary body and is connected releasably and reconnectably to the second subsidiary body via an adhesion zone. The cover is preferably fixedly connected only to the end of the first subsidiary body remote from the hinge-like connection and bears on the two subsidiary bodies for as long as the analytical aid is not in use. During use, the cover can be folded away at least from the second subsidiary body and the lancet tip, so that it does not get in the way of the use of the analytical aid and, after use, is again able to cover the whole of the base body, in order to accommodate the lancet in an inaccessible position. Preferred materials chosen for the cover are polyester or polycarbonate. A suitable thickness for the cover is 100 to 150 μm. It can have the same length as the base body or can be made longer than the base body so that, in the starting position, it protrudes beyond that end of the second subsidiary body remote from the hinge-like connection. In the starting position, the cover is connected to the second subsidiary body in a releasable manner by means of the adhesion zone. The adhesion zone can, for example, comprise an easily releasable and reconnectable adhesive layer to which the cover or second subsidiary body adheres. The adhesion zone can be arranged on the second subsidiary body or on the cover. By means of the cover, it is advantageously possible to avoid accidental injury to the user or contamination by residues of the sample.

According to another particular embodiment of the present invention, the means for transporting the sample is a capillary. A capillary in the form of a capillary gap can be formed, for example, by a structured spacer adhesive tape and a hydrophilic cover film which are secured on the second subsidiary body. However, the means for transport of the sample can also be any other suitable means known to the person skilled in the art, for example capillary-active material or a wick. In the analytical aid according to this embodiment, however, the sample can also spread from the sample application site to the test field with additional provision of a means for transporting the sample, for example in cases where the test field borders the sample application site and contains an absorbent material.

In another form thereof, the present invention provides a method for producing analytical aids of the type having first and second bodies hingedly connected to one another, with the first body carrying a lancet having a lancet tip and the second body carrying a test element. In this method, a first band of material from which the first bodies are formed is provided, and a second band of material from which the second bodies are formed is also provided. Pilot holes on the first band and the second band are aligned to orient the first band and the second band relative to one another. The first band and the second band are hingedly connected to one another (i.e., connected via a hinge-like connection), and the first and second bands are then separated into the analytical aids.

In certain embodiments of the invention, the bands should, on the one hand, be stiff enough to permit pivoting of the resulting subsidiary bodies for release of the lancet tip, and, on the other hand, they should be pliable or flexible enough to permit roll production. Suitable pliable bands are, for example, polyester films, e.g. the polyester film "Melinex" manufactured by DuPont Teijin Films, with a thickness of ca. 350 μm, or similar polymer films. The two pliable bands can be produced from one pliable band by cutting. The lancets and seals are secured on the first pliable band. The first pliable band is then rolled up and sterilized, in particular by radiation. Sterilization by radiation can be carried out, for example, with a dose of 25 kGray. After the lancets and the seals have each been secured on a section of the first pliable band and have been sterilized, and the test elements have each been secured on a section of the second pliable band, the two pliable bands can be connected to one another. In doing so, they have to be connected to one another with an exact fit. The bands are therefore held at an adjustable tensioning, which is controlled such that the pilot holes present in both bands always lie opposite one another within an admissible tolerance before the bands are connected to one another via a hinge-like connection, for example by an adhesive tape, to form a single pliable band. The seal is then secured at least with one edge to the second subsidiary body by adhesive bonding or welding. Thereafter, the individual analytical aids according to the invention are cut off from the band. The cut for separating the analytical aids is made centrally between two lancets and parallel to them. Before or after the separation of the analytical aids, the areas with the pilot holes can be removed, for example by cutting them off.

According to an embodiment of the invention, another possibility for producing the analytical aids from two pliable bands is one in which the sections of the first pliable band with the sealed and sterilized lancets and the sections of the second pliable band with the test elements are firstly individually separated and then respective sections of the two bands are connected to one another via hinge-like connections to in each case form one base body (if appropriate also using in each case at least one pilot hole).

According to a particular embodiment of the present invention, the seal of each individual analytical aid is, after separation, controlled in a vacuum to check its tightness, so that it is possible to detect any damage to the seal caused by the cut made for separating the analytical aids. To accomplish this, the individual analytical aids can be placed in a chamber in which a vacuum is created. The air enclosed by the seal increasingly swells the seal as the external pressure decreases. If a seal is damaged, it does not swell or it swells only incompletely. This can be recorded by an automatic image-processing system and evaluated. Defective analytical aids are rejected. By means of image evaluation, they can be examined for the cause of the defect. This permits rapid reaction to, and elimination of, the sources of the defects.

The finished analytical aids according to this embodiment can be packed individually or in groups into suitable containers or magazines. The magazine used can, for example, be a system of the kind described in U.S. Pat. No. 6,497,845. A person skilled in the art will be able to adapt such a magazine to the analytical aid according to the present invention.

The invention further relates to a method for analysis of a sample using an analytical aid according to the invention, comprising the following steps:

(a) inserting the analytical aid into an analysis device;

(b) pivoting the first and second bodies relative to one another from a starting position through an angle α, whereupon the seal is opened and the lancet tip protrudes beyond the first subsidiary body and is released for use;

(c) inserting the lancet tip into a sample collection location;

(d) pivoting the two bodies to return them to a starting position or into another sample application position;

(e) applying the sample from the sample collection location onto a sample application site of the analytical aid so that the sample reaches a test field of the analytical aid;

(f) analyzing the sample on the test field;

(g) optionally: ejecting a used analytical aid; and (g1) (alternative to (g)) guiding the used analytical aid back into a magazine.

In certain embodiments, the lancet tip in step (c) emerges from an opening of the analysis device, and the sample application site in step (e) emerges from the same opening.

BRIEF DESCRIPTION OF DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIGS. 3*a*-3*f* are cross-sectional views of the analytical aid of FIG. 1 and show a schematic representation of another possible mode of operation of the analytical aid.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
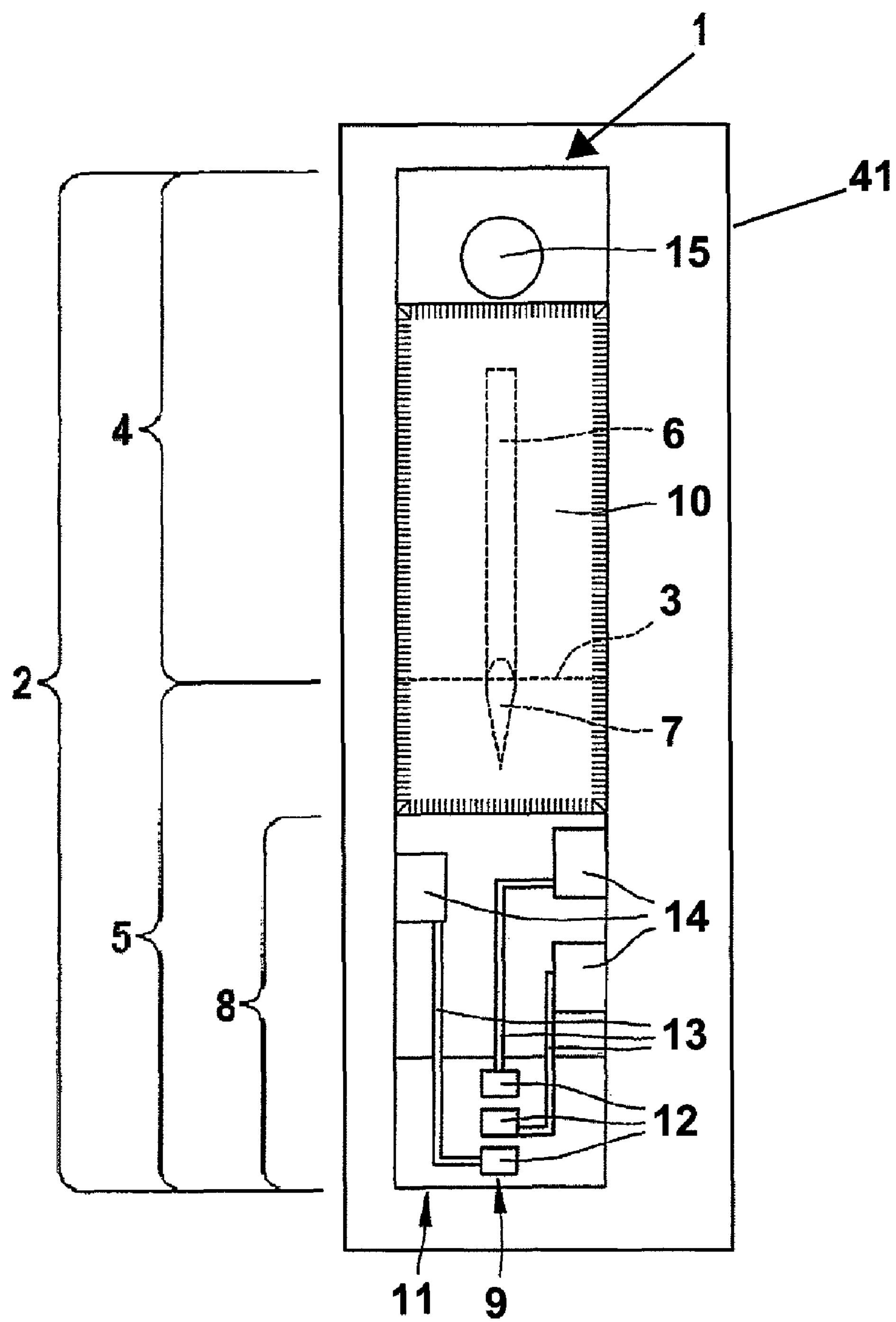
FIG. 1 shows a schematic representation of an analytical aid according to one embodiment of the invention.

With reference to FIG. 1, the analytical aid 1 comprises a base body 2 with two subsidiary bodies 4, 5 connected via a hinge-like connection 3. The first subsidiary body 4 carries a lancet 6, which has a lancet tip 7. The second subsidiary body 5 carries a test element 8, which comprises a test field (not shown). A means (not shown) for sample transport in the form of a capillary serves to transport a sample liquid from the sample application site 9 to the test field of the test element 8. The sample application site 9 is arranged in the area of an end 11 of the second subsidiary body 5 remote from the hinge-like connection 3.

FIG. 1 shows the analytical aid in the unused state or unused position. The two subsidiary bodies 4, 5 are therefore arranged in a common plane. The lancet 6 is protected by a seal 10. The seal 10 is fixedly connected to the first subsidiary body 4. It encloses the whole lancet 6 and in particular the lancet tip 7, which protrudes beyond the first subsidiary body 4 in the area of the hinge-like connection 3 and is oriented substantially parallel to the second subsidiary body 5. In the area of the lancet tip 7, the seal 10, which stretches across the hinge-like connection 3, is fixedly connected to the second subsidiary body 5.

When the analytical aid 1 is put to use, the two subsidiary bodies 4, 5 are pivoted relative to one another out of the plane about the hinge-like connection 3. Upon pivoting of the two subsidiary bodies 4, 5, the seal 10 is opened in the area of the lancet tip 7, such that the lancet tip 7 is released for use.

The test element 8 shown in FIG. 1 comprises means for electrochemical analysis in the form of electrodes 12, electrical tracks 13 and contact pads 14. The analytical aid 1 furthermore comprises a recess 15 in the first subsidiary body 4 for engagement of a guide element (not shown) in an analysis device via which the analytical aid 1 is guided to a sample collection location (for example the pad of a patient's finger) for puncture with the lancet 6 and application of the sample analytical aid 1 can be packed individually or in a suitable container or magazine 41, as depicted diagrammatically in FIG. 1.

FIGS. 2*a*-2*d* are a schematic representation of the mode of operation of an analytical aid according to the invention, in particular for puncture with the lancet and application of the sample.

An analytical aid 1 according to the invention is shown in cross section from the side in FIGS. 2*a*-2*d*. It comprises two subsidiary bodies 4, 5 which are connected via a hinge-like connection 3 to form a base body 2, the first subsidiary body 4 having a recess 15 for guiding the analytical aid 1. A lancet 6 secured on the first subsidiary body 4 is protected by a pocket-like seal 10 in the unused state (FIG. 2(*a*)). A flexible strip 16 hingedly connects the two subsidiary bodies 4, 5 to one another, i.e., serves as a hinge-like connection 3. A test element 8 arranged on the second subsidiary body 5 comprises a test field 17 which is connected to the sample application site 9 via a capillary gap serving as a means for sample transport 18. The broken line represents the skin level 20.

The possible sequence of a measurement, for example of blood glucose, is now described. An analytical aid is shown in the unused state (unused position) in FIG. 2*a*. The two subsidiary bodies 4, 5 are situated in one plane, and the lancet 6 is protected by the seal. The strip-shaped analytical aid 1 is inserted into a suitable measuring device (not shown), either as a single strip or in a magazine together with a multiplicity of strips. The device is pressed, for example with a cone, against a user's finger, as a result of which the device is switched on and the sequence can take place without any further user interaction. An analytical aid 1 according to the invention is released from a magazine and transported in the direction of the finger. If, instead of a magazine, a single analytical aid 1 is used, the sequence of movement is comparable.

Figures 2A, 2B, 2C, 2D:
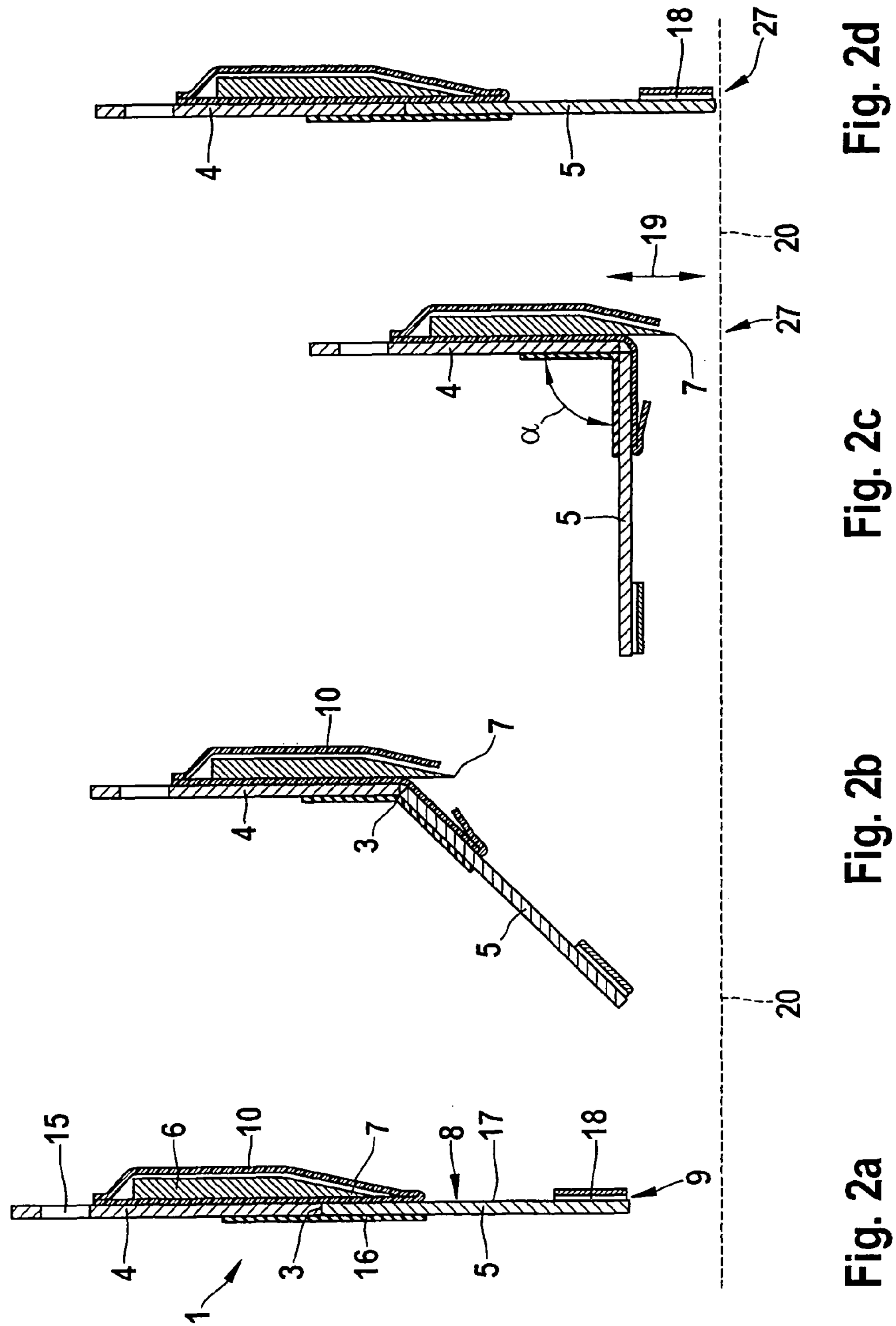
FIGS. 2*a*-2*d* are cross-sectional views of the analytical aid of FIG. 1 and show a schematic representation of a mode of operation of the analytical aid.

FIG. 2*b* shows the pivoting of the two subsidiary bodies 4, 5 about the hinge-like connection. The strip-shaped analytical aid 1 is bent off at a defined location (the hinge-like connection 3). The bending is achieved by the fact that the analytical aid 1 is bent, during transport in the device, by a tilting movement of a closure cap, or by some other force acting on the bend location. The lancet tip 7 cuts through the sterile protective sleeve serving as seal 10.

FIG. 2*c* shows the analytical aid 1 upon puncture with the lancet tip 7, the subsidiary bodies 4, 5 being pivoted relative to one another by an angle $\alpha=90°$. As soon as the strip is bent by at least 90°, the lancet tip 7 protrudes past the strip contour. By means of a rapid forwards/backwards movement of the strip in the arrow direction 19, the lancet tip 7 is pushed from an opening (not shown) of the device into the skin of the finger. This rapid movement can be effected by a spring mechanism, by a magnet actuator or by a motor drive, if appropriate in connection with a balance weight. After the puncturing procedure, the strip is drawn back into the device such that it is present once again in the unbent state.

FIG. 2*d* shows the application of the sample. To accomplish this, the path within the device is altered, for example by a switching arrangement, so that the strip, when pushed out again in the unbent state, emerges from the device with the opening of the capillary 18. In this way, the absorbent sample application site exactly impinges on a droplet of blood that has emerged in the meantime from the skin. At the end of the emerge movement, the contact pads on the strip are contacted by the measurement electronics (not shown). This is effected by slide contacts or point contacts. In the case of optical evaluation, for example, the reflection measurement starts. As soon as the sample volume has been absorbed, the strip can be drawn back again into the device. Interference with the measurement caused by movements is thus suppressed. The user can receive an acoustic signal indicating that he may take the device away from the finger. The measurement of an optical change, of an electrical current or of an electrical potential at the same time takes place comparable to the measurement in conventional test strips. At the end of the measurement, the used analytical aid 1 can be ejected or can be drawn back into a magazine. The sample application site in the analytical aid according to the invention can be arranged, for example, on that end of the second subsidiary body directed away from the hinge-like connection or on a long side of the second subsidiary body.

The method according to these teachings may therefore proceed as follows:

(a) inserting an analytical aid 1 into an analysis device, (b) pivoting the two subsidiary bodies 4, 5 towards one another from a starting position through an angle $\alpha$, whereupon the seal 10 is opened and the lancet tip, protruding beyond the first subsidiary body 4, is released for use, (c) inserting the lancet tip 7 into a sample collection location 27 (see below for example, FIG. 3), (d) applying the sample from the sample collection location 27 onto the sample application site 9 of the analytical aid 1 so that the sample reaches the test field 17, and (e) analysing the sample on the test field 17.

In step (c), the lancet tip 7 emerges from an opening 39 (see below for example, FIG. 6) of the analysis device, and, in step (e), the sample application site 9 emerges from the same opening 39. In step (d) of the method according to the invention, the two subsidiary bodies 4, 5 are preferably pivoted in such a way that they are located (in the same way as in the unused state) in a common plane (unbent strip). In this sample application position, which can correspond to the starting position, the sample at the sample application site is placed onto the analytical aid 1 according to the invention.

FIGS. 3*a*-3*f* show a schematic representation of another mode of operation of an analytical aid, particularly for puncture with the lancet tip and the application of the sample. The analytical aid 1 according to the invention shown in FIGS. 3*a*-3*f* corresponds in structure to the analytical aid shown in FIGS. 2*a*-2*d*.

Figure 3A:
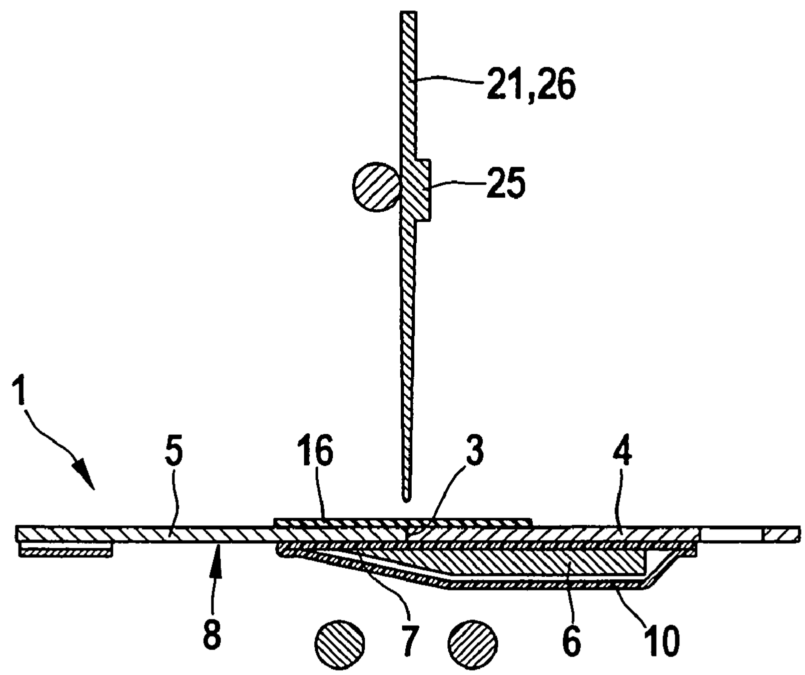

In FIG. 3*a*, the analytical aid 1 is located in a starting position in an analysis device in which the two subsidiary bodies 4, 5 are arranged in one plane. The seal 10 is intact. A slide 21 belonging to the analysis device is arranged above the hinge-like connection 3.

Figure 3B:
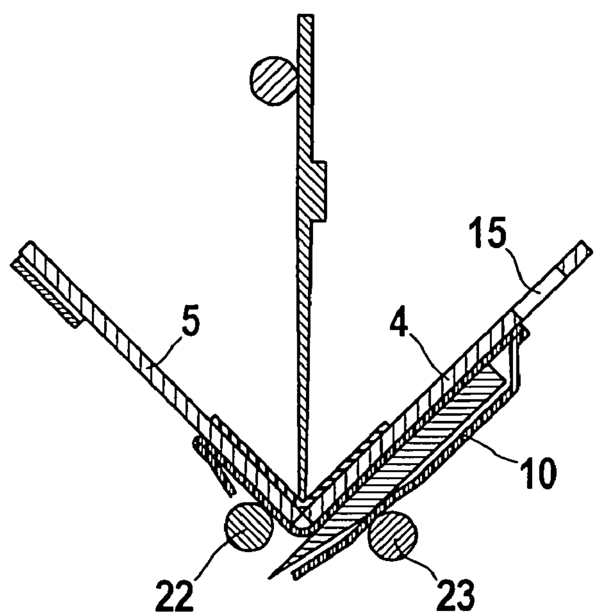

FIG. 3*b* shows the pivoting of the two subsidiary bodies 4, 5 towards one another from the starting position. The slide 21 exerts a force from above on the base body 2 of the analytical aid 1 in the area of the hinge-like connection 3. At the same time, the two subsidiary bodies 4, 5 lie, at a certain distance from the hinge-like connection 3, in each case on a deflector 22, 23. The strip-shaped analytical aid 1 in this way bends at the hinge-like connection. The seal 10 is opened, and the lancet tip 7, protruding beyond the first subsidiary body 4, is released.

Figure 3C:
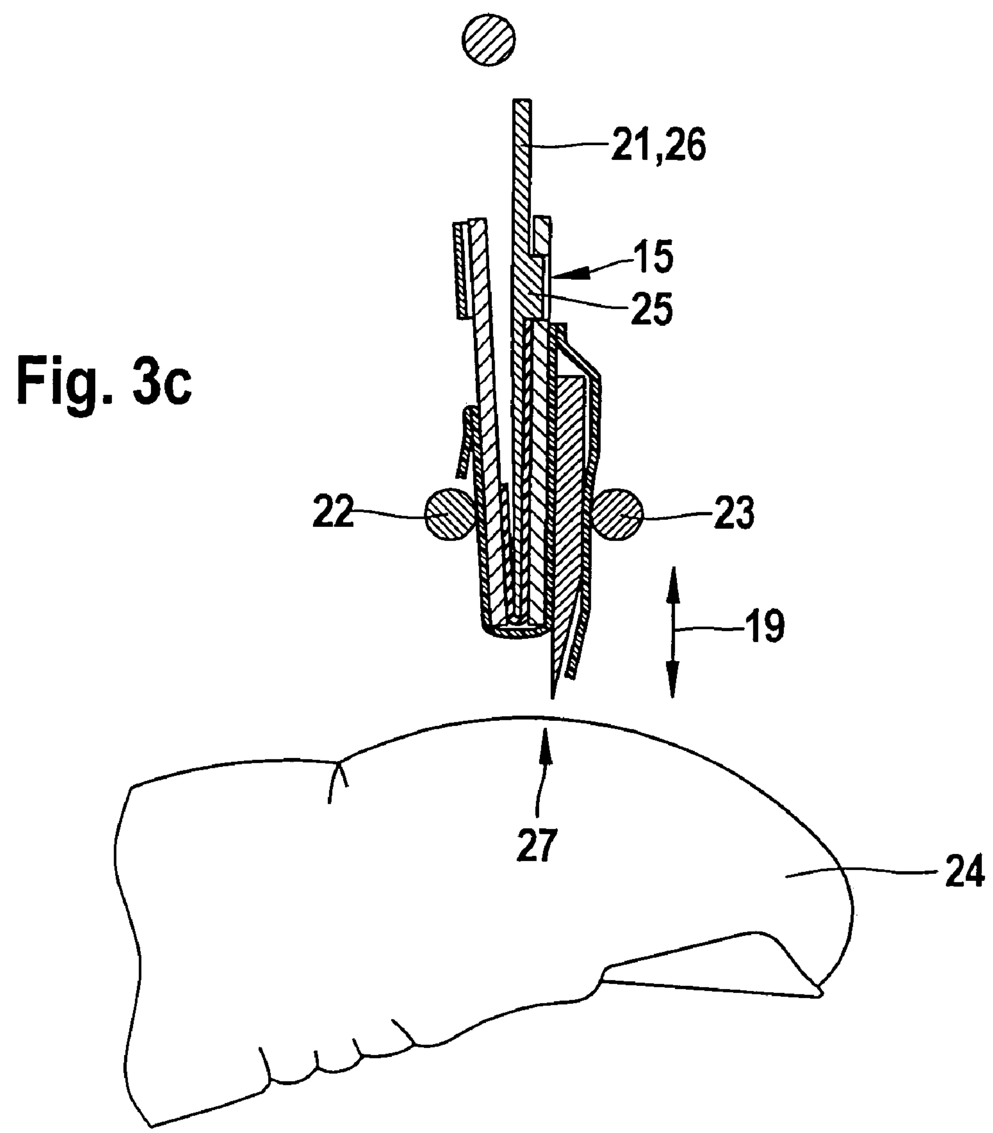

FIG. 3*c* shows the lancet tip 7 puncturing a finger 24 of a patient. Here, the two subsidiary bodies 4, 5 are pivoted through almost $\alpha=180°$ relative to the starting position. The slide 21 has a projection 25, which, in this position, engages in the recess 15 in the first subsidiary body 4. During insertion of the lancet tip 7 into the finger 24, and in the subsequent steps, the slide 21 serves as a guide element 26 via which the analytical aid 1 is guided to the sample collection location 27 for puncture with the lancet 6 and for application of the sample. The puncture into the sample collection location 27 on the finger 24 takes place in direction of movement 19.

FIG. 3*d* shows the return movement of the analytical aid 1 after the puncture procedure. It is drawn back until a further deflector 28 is pushed between the two folded-together subsidiary bodies 4, 5, and these are pivoted apart again. In doing so, the first subsidiary body 4 remains connected to the slide 21 through the engagement of the projection 25 in the recess 15.

Figure 3E:
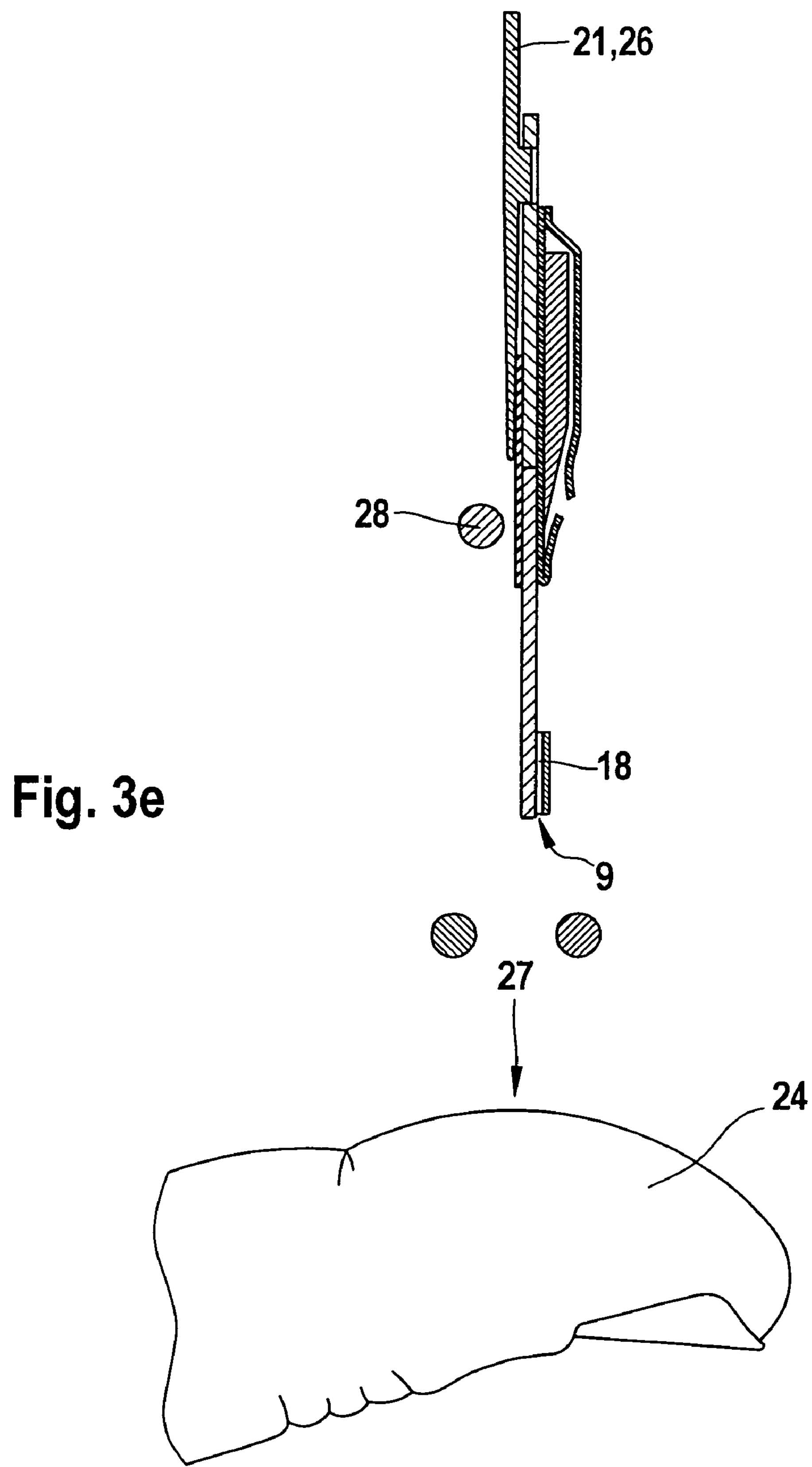

In FIG. 3*e*, the subsidiary bodies 4, 5 have been pivoted into a sample application position in which the subsidiary bodies 4, 5 are located in one plane and the analytical aid 1 is perpendicular to the starting position shown in FIG. 3*a*.

Figure 3F:
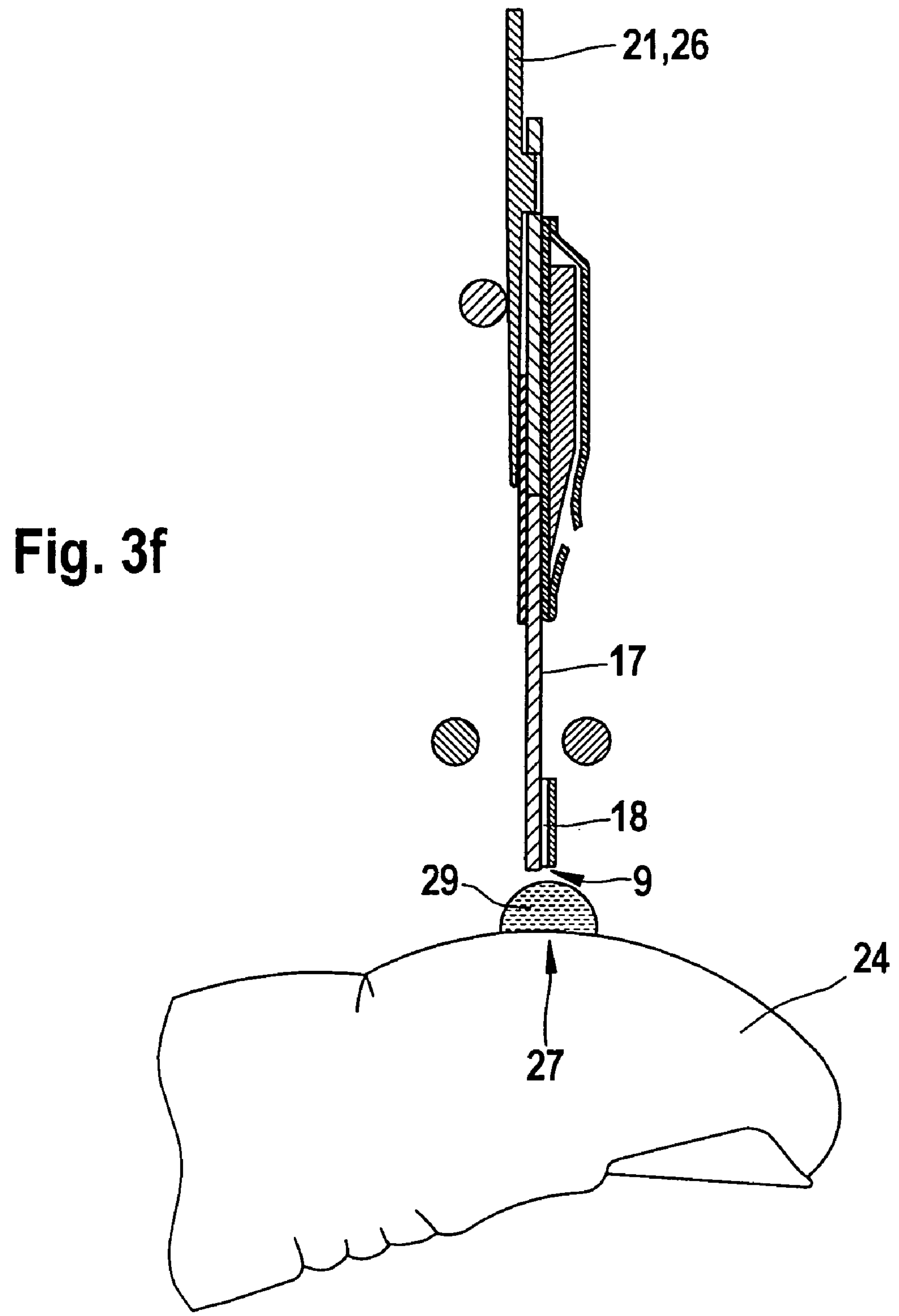

FIG. 3*f* shows the sample application. The sample application site 9 on the test element 8 is brought to the sample collection location 27 on the finger 24 where a blood droplet 29 has formed. The blood is taken up at the sample application site 9 and transported with the aid of the capillary 18 to the test field 17 where the sample is analysed, as has been described above with reference to FIGS. 2*a*-2*d*.

FIGS. 4 to 11 are schematic representations of a sequence of movements of an analytical aid in an analysis device. The analytical aid is shown in section. The structure of the analytical aid 1 corresponds substantially to the structure of the analytical aids 1 described with reference to FIGS. 2 and 3, with the difference being that it additionally has a cover 30 which is arranged on the analytical aid 1. The cover 30 is fixedly connected at one end 31 to the first subsidiary body 4. The cover 30 is connected releasably and reconnectably to the second subsidiary body 5 via an adhesion zone 32. The cover 30 protects against inadvertent injury by the lancet 6, in particular after use of the analytical aid 1.

Figure 4:
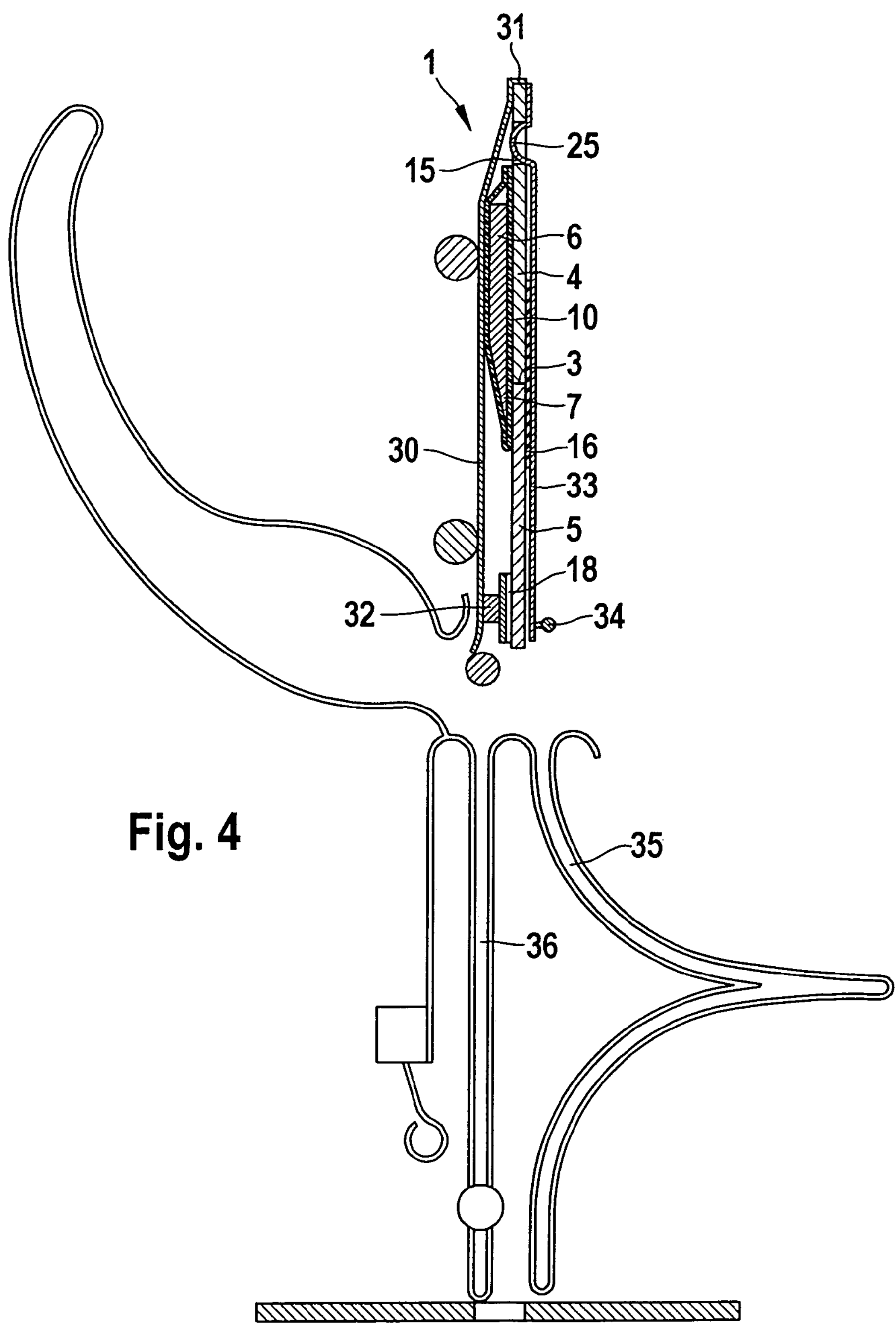
FIGS. 4 to 11 are various cross-sectional schematic views that show a sequence of movement of an analytical aid according to the invention in an analysis device.

FIG. 4 shows the analytical aid 1 in its starting position within a schematically depicted analysis device. The strip-shaped analytical aid 1 is, for example, inserted manually into the device through a slit. The opening of the slit is markedly greater than the cross section of the strip and narrows to a cross section through which the analytical aid 1 can still pass without any appreciable friction. This ensures easy handling, and the user has no difficulty in finding the opening. However, it is necessary to insert the strip in the correct orientation. For this purpose, large, clear markings can be printed onto the top face of the analytical aid 1. Suitable optical or mechanical or other sensors can be mounted in the analysis device to trigger a warning signal if the orientation is wrong or to block the insertion of the strip. In the slit, the strip is guided a short distance (for example 5 mm) in a straight line. This is intended to ensure that the analytical aid 1 is correctly aligned for the subsequent steps, regardless of the angle at which it has been inserted into the slit. In the starting position according to FIG. 4, the analytical aid 1 is fitted into a holder 33 in the analysis device. The holder 33 comprises a projection 25 that engages in the recess 15. Moreover, the holder 33 has a carrier element 34 which can interact with guide rails 35, 36 in the analysis device. The holder 33 can also be bent in the area in which the inserted analytical aid 1 has the hinge-like connection 3. In the starting position of the analytical aid 1 in the analysis device, the two subsidiary bodies 4, 5 of the analytical aid 1 are arranged in a common plane, and the cover 30 covers the analytical aid 1 completely on one side.

Figure 5:
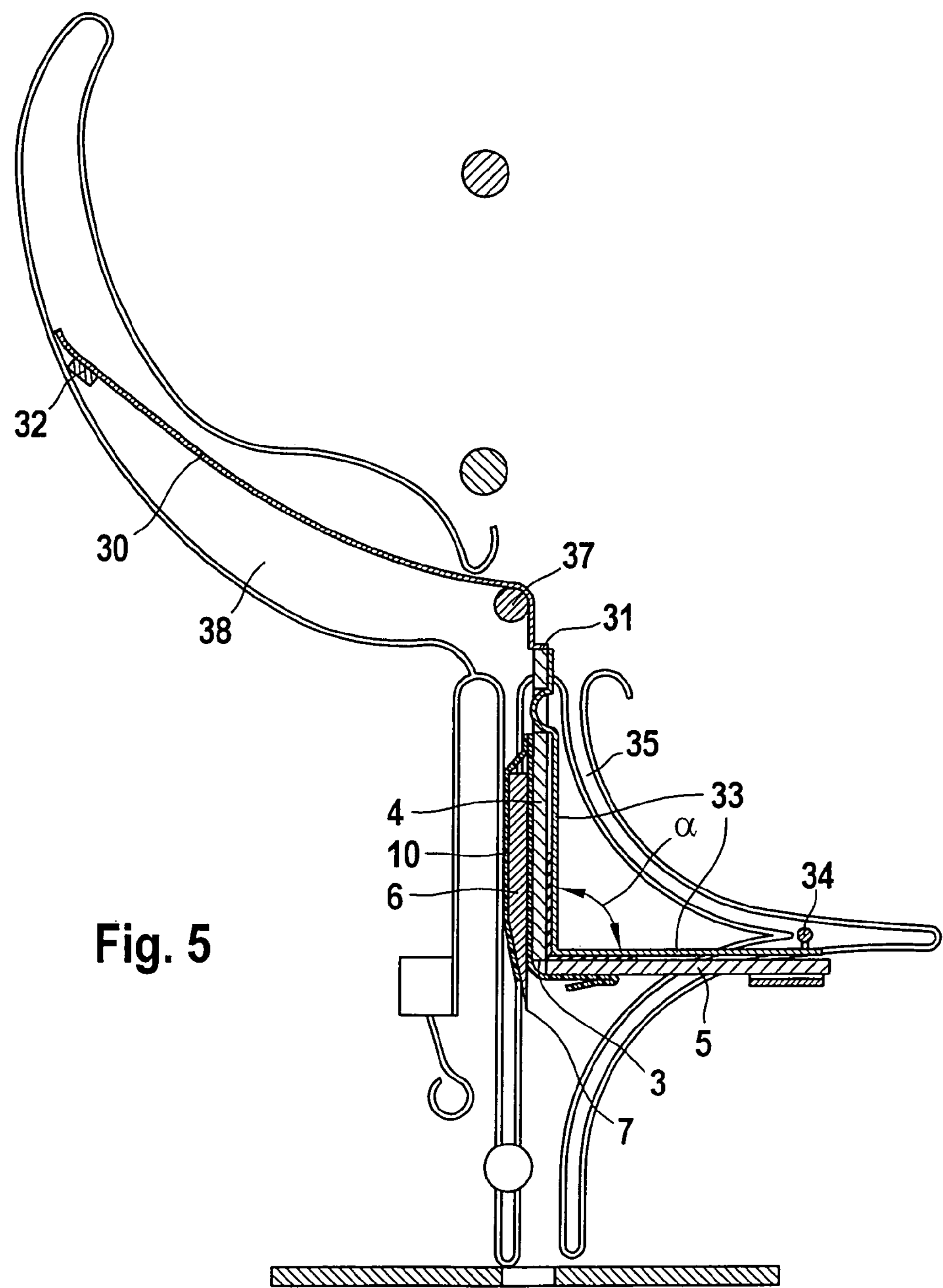

FIG. 5 shows the movement of the analytical aid 1 from the starting position in the direction to the sample collection location. The carrier 34 runs along the first guide rail 35, which is designed such that the subsidiary bodies 4, 5 of the analytical aid 1 that are held in the holder 33 are pivoted relative to one another. In FIG. 5, they have already moved through an angle of $\alpha=90°$ from the starting position. By means of the lancet tip 7, the lancet 6 has opened the seal 10, and the lancet tip 7 protrudes beyond the first subsidiary body 4. While the subsidiary bodies 4, 5 are pivoted and the lancet tip 7 is released, the cover 30 is guided via a guide element 37 laterally away from the base body 2 into a separate channel 38. For this purpose, the cover 30 together with adhesive zone 32 is detached from the analytical aid 1, such that it is now connected to the first subsidiary body 4 only at the end 31.

The cover 30 can be guided such that it exerts a spring action which presses the base body 2 of the analytical aid 1 against a limit stop present in the analysis device, or which ejects the analytical aid 1 after completion of the measurement procedure.

Figure 6:
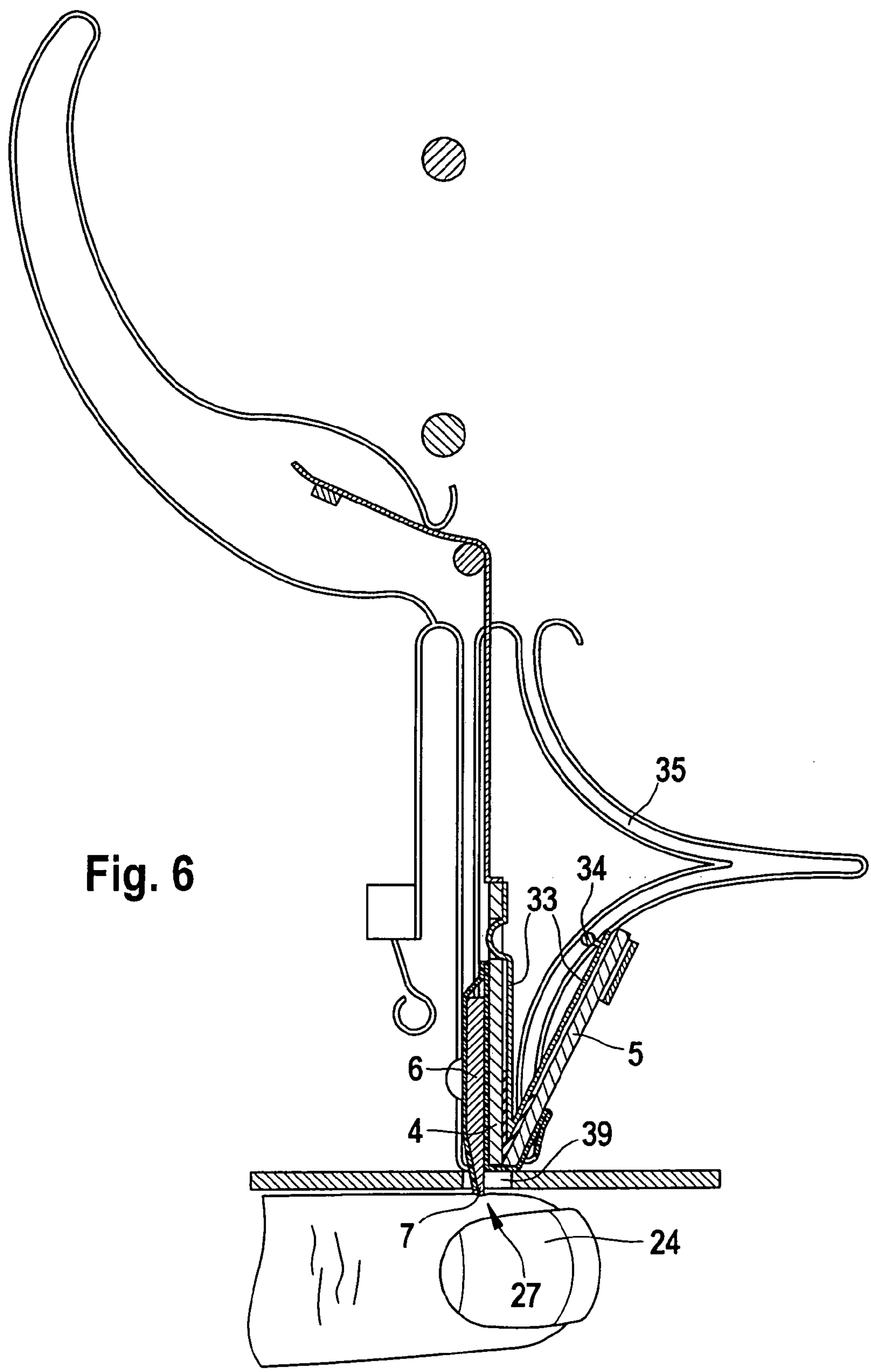

FIG. 6 shows the lancet tip 7 puncturing a finger 24. To do this, the carrier 34 runs further in the first guide rail 35 and carries the holder 33 and analytical aid 1 with it, such that the two subsidiary bodies 4, 5 are pivoted by up to an angle of about 140° from the starting position. The lancet tip 7 emerges from the opening 39 of the analysis device and punctures the skin of the finger 24.

Figure 7:
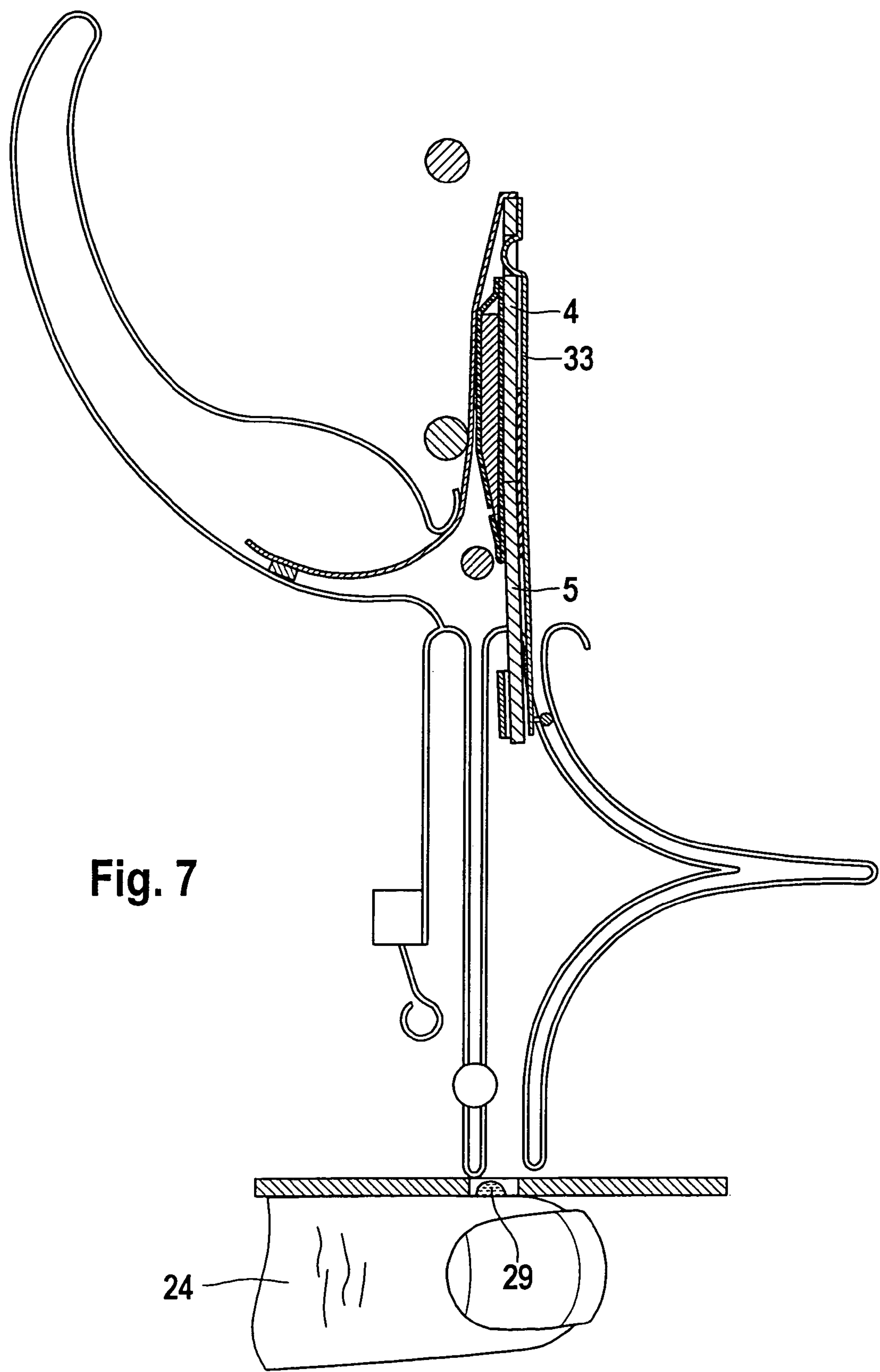

According to FIG. 7, after the puncturing procedure, the analytical aid 1 is drawn back until the two subsidiary bodies 4, 5 are once again located in a common plane and the holder 33 is unbent. In the meantime, a blood droplet 29 forms on the finger 24.

Figure 8:
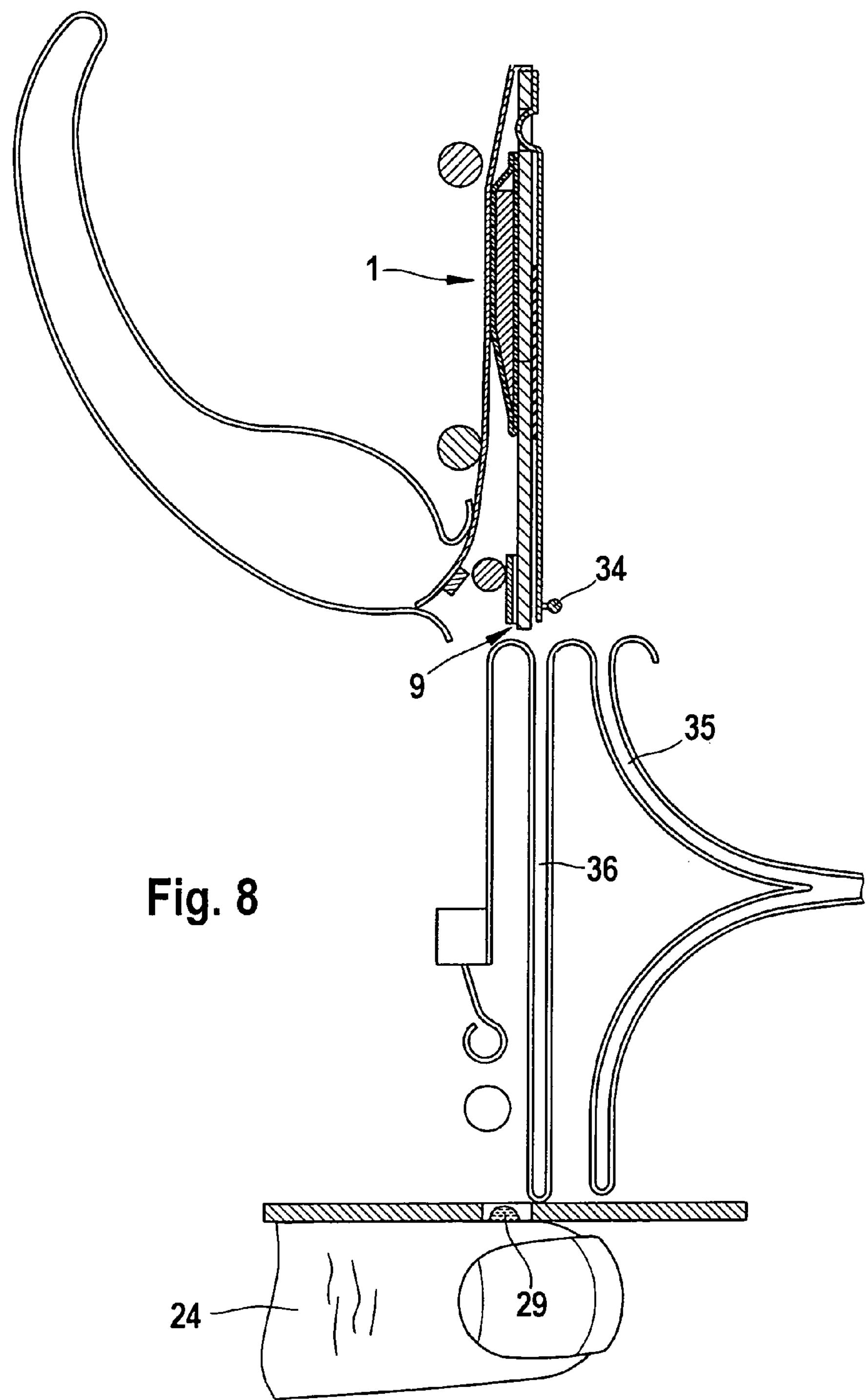
Figure 9:
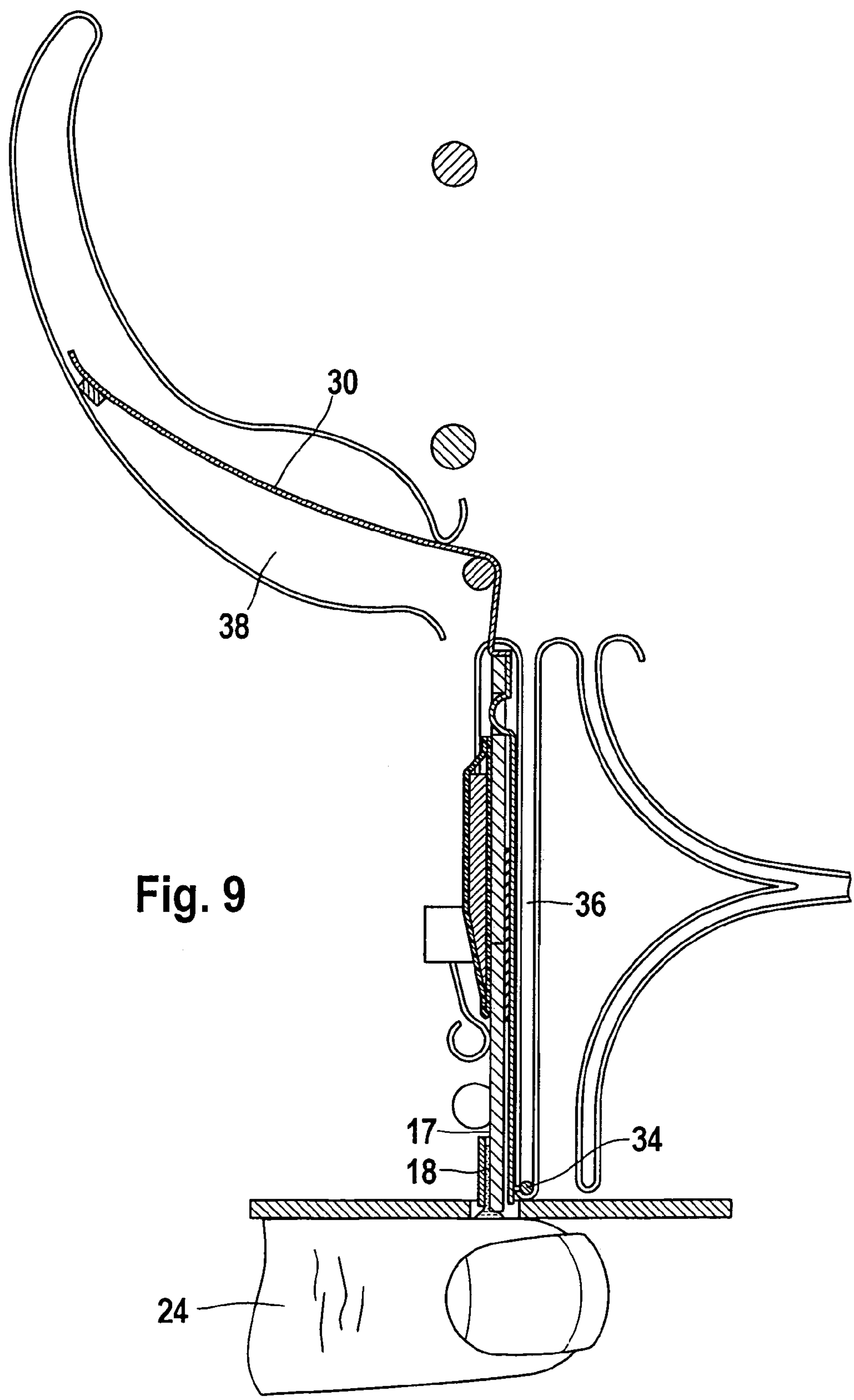

FIGS. 8 and 9 show how the analytical aid 1 is moved in the analysis device for application of a sample. The carrier 34 is moved out of the first guide rail 35. The analytical aid 1 in the analysis device is shifted laterally (for example by means of a switching arrangement) into a new position shown in FIG. 8. The sample application site 9 is then moved to the finger 24, the carrier 34 being guided in the second guide rail 36. Upon application of the sample (FIG. 9), which takes place through the opening 39 in the analysis device, the blood sample ascends in the capillary means for sample transport 18 until it reaches the test field 17. During the sample application, the cover 30 is folded away from the analytical aid 1 and positioned in the channel 38.

Figure 10:
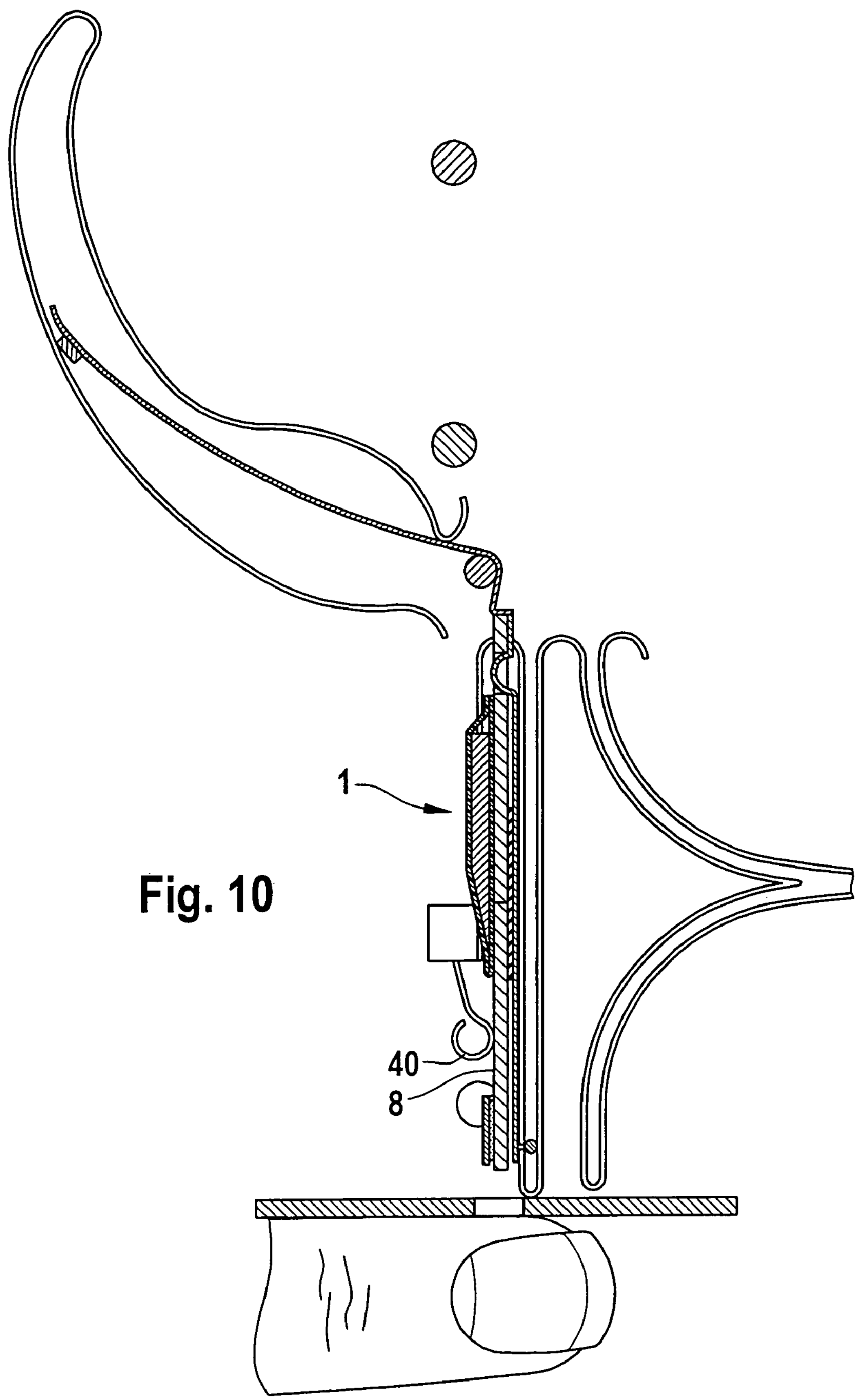

FIG. 10 shows the analytical aid 1 in a measurement position. To carry out an electrochemical analysis, the analytical aid 1 is drawn back after the sample application, until an electrical contact 40 sits on the contact pad (not shown) provided for this purpose on the test element 8. A measurement is carried out in this position.

Figure 11:
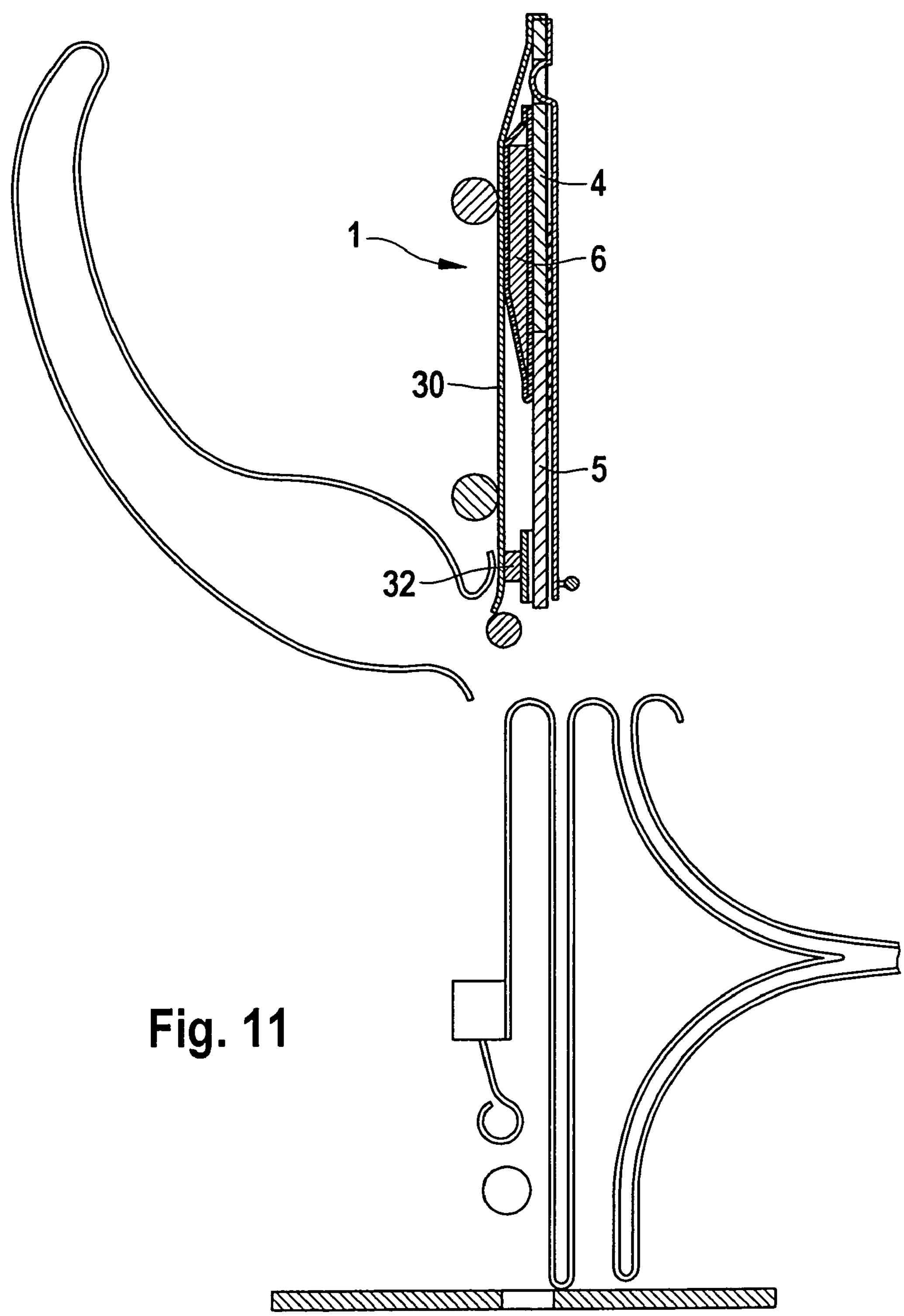

After the measurement, the analytical aid 1 is moved back into the starting position, as is shown in FIG. 11. The cover 30 is secured on the second subsidiary body 5 by means of the adhesion zone 32, so that a user is protected against inadvertently touching the lancet 6 and from contamination by sample residues on the used analytical aid 1.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS

| | |
|---|---|
| 1 | analytical aid |
| 2 | base body |
| 3 | hinge-like connection |
| 4 | first subsidiary body |
| 5 | second subsidiary body |
| 6 | lancet |
| 7 | lancet tip |
| 8 | test element |
| 9 | sample application site |
| 10 | seal |
| 11 | end of the second subsidiary body |
| 12 | electrodes |
| 13 | electrical tracks |
| 14 | contact pads |
| 15 | recess |
| 16 | flexible strip |
| 17 | test field |
| 18 | means for sample transport, capillary |
| 19 | direction of movement |
| 20 | skin level |
| 21 | slide |
| 22 | first deflector |
| 23 | second deflector |
| 24 | finger |
| 25 | projection |
| 26 | guide element |
| 27 | sample collection location |
| 28 | third deflector |
| 29 | blood droplet |
| 30 | cover |
| 31 | end of cover |
| 32 | adhesion zone |
| 33 | holder |
| 34 | carrier |
| 35 | first guide rail |
| 36 | second guide rail |
| 37 | guide element |
| 38 | channel |
| 39 | opening |
| 40 | electrical contact |

What is claimed is:

1. An analytical aid for puncturing a body part and analyzing a body fluid sample, comprising:

first and second bodies hingedly connected to one another, the first body carrying a lancet having a lancet tip and the second body carrying a test element having a test field and a sample application site;

the analytical aid having an unused position in which the first and second bodies are arranged substantially in a common plane and in which the lancet is protected by a seal connected to the first body and is separated from the test field;

the first and second bodies being pivotable relative to one another from the unused position; and wherein, pivoting the first and second bodies from the unused position causes the seal to open to release the lancet tip for use.

2. The analytical aid of claim 1, further comprising a flexible strip that hingedly connects the first body and the second body.

3. The analytical aid of claim 1, wherein the sample application site is positioned on the second body remote from the position of the connection of the first body and the second body.

4. The analytical aid of claim 1, wherein the lancet tip protrudes beyond the first body in the position of the connection of the first body and the second body.

5. The analytical aid of claim 1, wherein the lancet tip is oriented substantially parallel to the second body in the unused position of the analytical aid.

6. The analytical aid of claim 1, wherein the seal comprises a pocket which at least partially encloses the lancet when the analytical aid is in the unused position.

7. The analytical aid of claim 1, wherein the seal at the lancet tip is fixedly connected to the second body.

8. The analytical aid of claim 1, wherein the first body and the second body are hingedly connected by the seal.

9. The analytical aid of claim 1, wherein the test element comprises means for electrochemical or optical analysis of a sample present on the test field.

10. The analytical aid of claim 1, wherein the first body has a recess configured to engage a guide element of an analysis device.

11. The analytical aid of claim 1, further comprising a cover fixedly connected to the first body and releasably and reconnectably connected to the second body via an adhesion zone.

12. The analytical aid of claim 1, further comprising a means for capillary transport of a fluid sample from the sample application site to the test field.

13. The analytical aid of claim 1, further comprising a magazine which houses the analytical aid.

14. The analytical aid of claim 1, wherein the seal is connected to the second body in the unused position.

15. The analytical aid of claim 1, wherein the first and second bodies are pivotable relative to one another from the unused position to a second position in which the lancet is configured to puncture a body part.

16. An analytical aid for puncturing a body part and analyzing a body fluid sample, comprising:

first and second bodies hingedly connected to one another, the first body carrying a lancet having a lancet tip and the second body carrying a test element having a test field and a sample application site;

the analytical aid having an unused position in which the first and second bodies are arranged substantially in a common plane and in which the lancet is protected by a seal connected to the first and second bodies and is separated from the test field;

the first and second bodies being pivotable relative to one another from the unused position; and the seal opening to release the lancet tip during pivoting of the first and second bodies relative to one another.

17. The analytical element of claim 16, wherein pivoting the first and second bodies causes the seal to open.

18. The analytical aid of claim 16, wherein the sample application site is positioned on the second body remote from the position of the connection of the first body and the second body.

19. The analytical aid of claim 16, wherein the lancet tip protrudes beyond the first body in the position of the connection of the first body and the second body.

20. The analytical aid of claim 16, wherein the lancet tip is oriented substantially parallel to the second body in the unused position of the analytical aid.

21. The analytical aid of claim 16, wherein the seal comprises a pocket which at least partially encloses the lancet when the analytical aid is in the unused position.

22. The analytical aid of claim 16, wherein the first body and the second body are hingedly connected by the seal.

23. The analytical aid of claim 16, wherein the first body has a recess configured to engage a guide element of an analysis device.

24. The analytical aid of claim 16, further comprising a cover fixedly connected to the first body and releasably and reconnectably connected to the second body via an adhesion zone.

25. The analytical aid of claim 16, wherein the first and second bodies are pivotable relative to one another from the unused position to a second position in which the lancet is configured to puncture a body part.

* * * * *